US00PP18312P3

(12) United States Plant Patent
Peters

(10) Patent No.: US PP18,312 P3
(45) Date of Patent: Dec. 11, 2007

(54) ***CORTADERIA* PLANT NAMED 'EVITA'**

(50) Latin Name: *Cortaderia selloana*
Varietal Denomination: Evita

(76) Inventor: Klaus Peters, Drüllerweg 14, Kranenburg (DE), D-47559

( * ) Notice: Subject to any disclaimer, the term of this patent is extended or adjusted under 35 U.S.C. 154(b) by 154 days.

(21) Appl. No.: 11/304,048

(22) Filed: Dec. 15, 2005

(65) Prior Publication Data

US 2007/0143898 P1 Jun. 21, 2007

(51) Int. Cl.
*A01H 5/00* (2006.01)

(52) U.S. Cl. ..... Plt./384

(58) Field of Classification Search ..... Plt./384
See application file for complete search history.

*Primary Examiner*—Wendy C. Haas
*Assistant Examiner*—Georgia Helmer
(74) *Attorney, Agent, or Firm*—Penny J. Aguirre

(57) ABSTRACT

A new cultivar of *Cortaderia selloana* named 'Evita', characterized by its short stature, its showy plumes of silvery white flowers, its vigorous growth habit, and its ability to flower as a young plant. 'Evita' is a *Cortaderia* that is suitable for small borders, larger containers, and for use as a dried and fresh cut flower.

2 Drawing Sheets

Botanical classification: *Cortaderia sellonana.*
Varietal denomination: 'Evita'.

BACKGROUND OF THE INVENTION

The present invention relates to a new and distinct cultivar of *Cortaderia selloana* and will be referred to hereafter by its cultivar name, 'Evita'. 'Evita' represents a new cultivar of pampas grass, a perennial ornamental grass grown for landscape use.

The inventor discovered and the new cultivar as a culm sport of *Cortaderia selloana* 'Pumula' (not patented) in a cultivated area of his nursery in 1998.

The new cultivar, 'Evita', was selected as unique in comparison to its parent, 'Evita', for its shorter height, its vigorous growth habit, and its ability to flower as a younger plant.

Asexual reproduction of the new cultivar was first accomplished by culm division in spring of 2000 in Kranenburg, Germany by the inventor. The characteristics of this cultivar have been determined to be stable and are reproduced true to type in successive generations.

SUMMARY OF THE INVENTION

The following traits have been repeatedly observed and represent the characteristics of the new cultivar. The new *Cortaderia* has not been observed under all possible environmental conditions. The phenotype may vary somewhat with variations in temperature, day-length, light intensity, soil types, and water and fertility levels without, however, any variance in genotype. The general observations, and descriptions that follow describe plants that were grown outdoors in a trial field in Kranenburg, Germany for a period of seven years.

1. 'Evita' is shorter in height in comparison to other cultivars of *Cortaderia selloana.* 'Evita' reaches about 120 m in height (under 4 feet), the parent plant 'Pumila' typically reaches up to 180 cm in height. 'Evita' is useful in smaller borders and larger containers, applications that are typically not suitable for *Cortaderia selloana.*
2. 'Evita' is very free flowering and blooms with white inflorescences from early August until late October in Germany.
3. The inflorescences of 'Evita' are suitable for cutting for floral arrangements.
4. 'Evita' flowers as a young plant with blooms arising on plants six months from culm division.
5. 'Evita' has a more vigorous grower in comparison to 'Pumila'.

BRIEF DESCRIPTION OF THE DRAWING

The accompanying colored photographs illustrate the overall appearance and distinct characteristics of the new *Cortaderia.*

The photograph in FIG. 1 was taken in early fall and illustrates the overall habit and appearance of a three year-old plant of 'Evita'.

Figure 1:
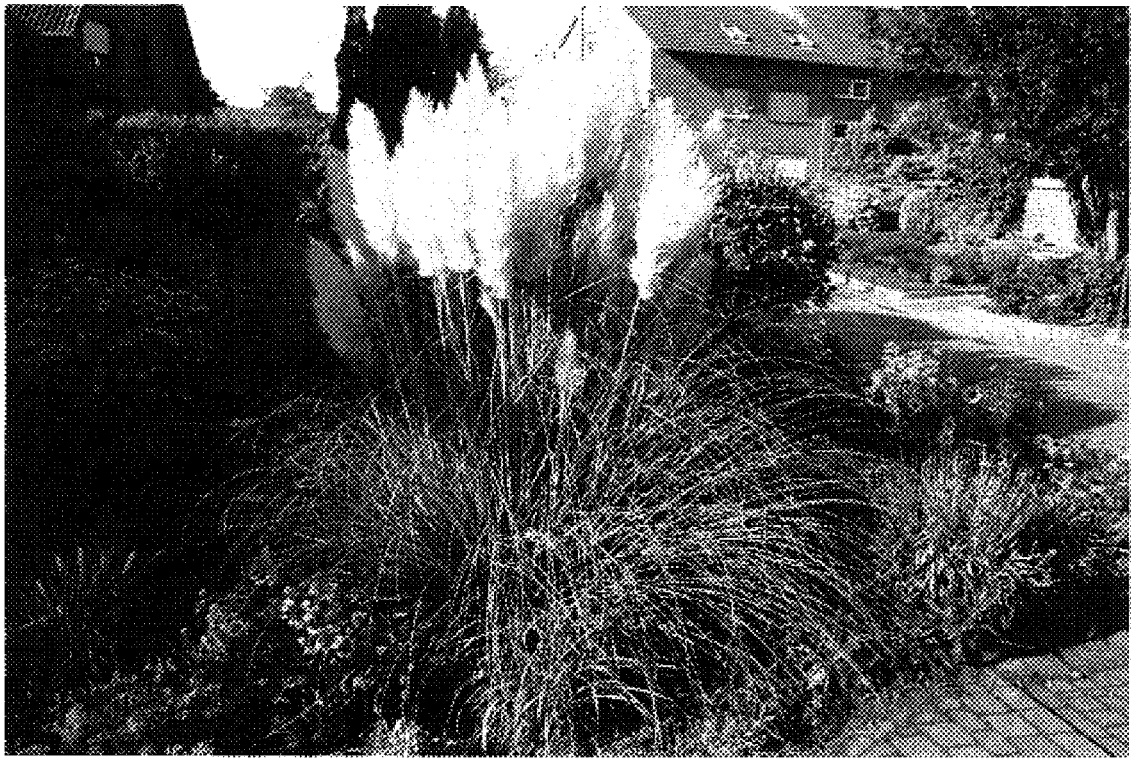
Figure 2:
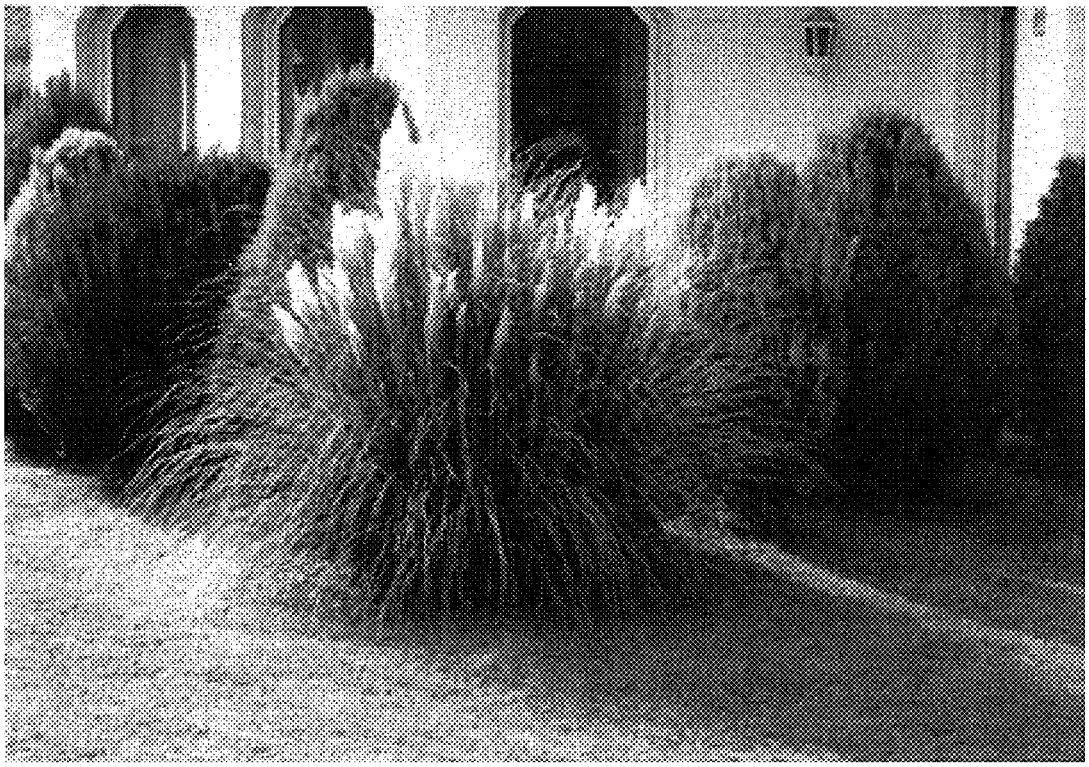

The photograph in FIG. 2 was taken in late summer of a three-year plant of 'Evita'.

Figure 3:
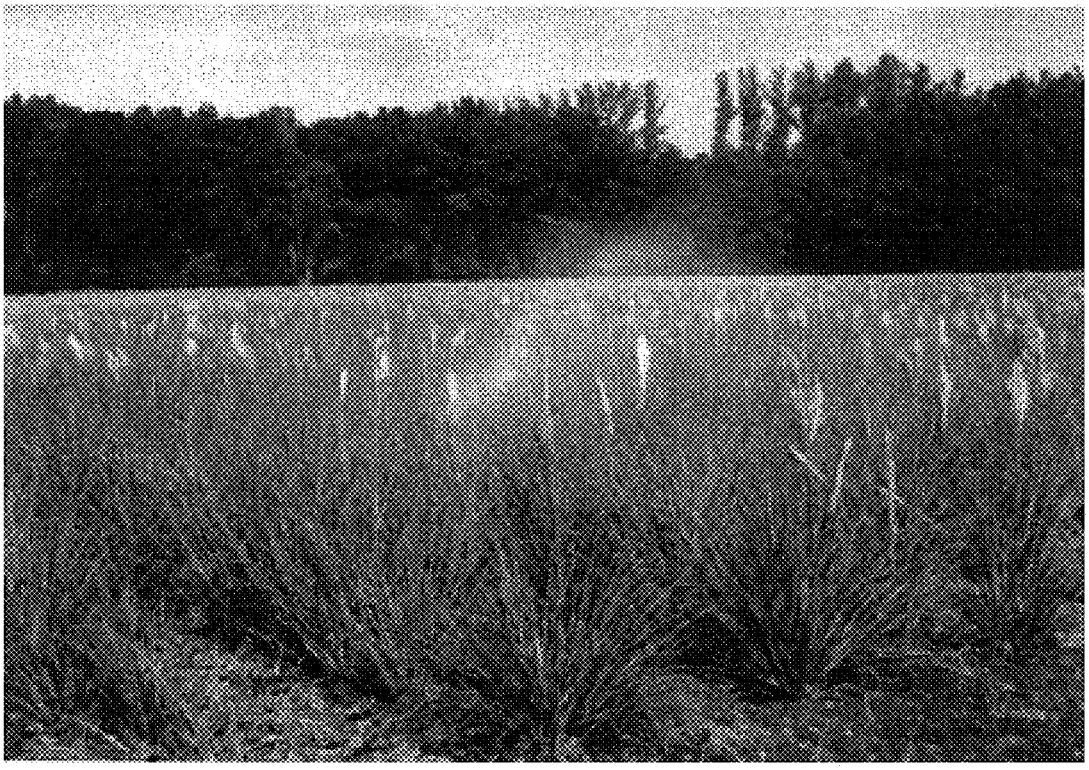

The photograph on FIG. 3 provides a view of a field planting of 'Evita' taken six months after planting culm divisions.

The colors in the photographs are as close as possible with the photographic and printing technology utilized. The color values cited in the detailed botanical description accurately describe the colors of the new *Cortaderia.*

DETAILED BOTANICAL DESCRIPTION

The general observations and descriptions describe plants that were grown outdoors under field conditions in Kranenburg, Germany and observed for a period of seven years. The detailed botanical description was taken from field grown plants two-years in age. The color determinations are in accordance with The 2001 R.H.S. Colour Chart of The Royal Horticultural Society, London, England, except where general color terms of ordinary dictionary significance are used.

Botanical classification: 'Evita' is a cultivar of *Cortaderia selloana.*

Common name: Evita Japanese pampas grass.

Parentage: Naturally occurring culm sport of *Cortaderia selloana* 'Pumila'.

General description:

*Blooming period.*—Bloom from early August to late October.

*Plant habit.*—Herbaceous, tussock-forming, ornamental grass with stout culms and leaf blades that cascade in a vase-shaped form with upright showy inflorescences.

*Height and spread.*—Reaches a height of about 1.2 m (4 ft) and a spread of about 1.5 m (5 ft) in three years of growth from a culm division.

*Cold hardiness.*—At least U.S.D.A. Zone 7, testing in not complete in colder zones.

*Culture.*—Grows best in fertile, reasonably moist soil in full sun, drought tolerant once established.

*Diseases and pests.*—*Cortaderia selloana* is typically disease free. No susceptibility or resistance to diseases or pests has been observed for 'Evita'.

*Root description.*—Fibrous, deep rooted.

Growth and propagation:

*Propagation.*—Culm division, best divided in late winter or early spring.

*Time required for root development from a single division.*—Roots will fully develop in a 10 liter container in about 9 months.

*Time required to produce a blooming size division.*—About six months when field grown from a culm division.

*Growth rate.*—Very vigorous, increases about 20 cm per month during spring growth.

Culm (stem) description:

*General.*—Rounded, enclosed by leafs sheathed to base.

*Culm aspect.*—Held upright to about a 45° angle.

*Culm color.*—147C, tinted at base with 200B.

*Culm size.*—Up to about 6.5 mm wide and 26 cm in height.

*Culm surface.*—Glabrous.

*Culm number.*—About 28 on a two-year-old plant.

*Internode length.*—Average of 4.5 cm.

*Ligule.*—Comprised of tuft of silky hairs, 2 mm in length, too fine to color define.

Foliage description:

*Leaf shape.*—Linear.

*Leaf division.*—Simple.

*Leaf base.*—Sheathed.

*Leaf arrangement.*—Alternate.

*Leaf apex.*—Acuminate.

*Leaf aspect.*—Emerging leaves are erect, leaf blades diverge from leaf sheath at ligule at about a 40° angle from center of culm and then cascade.

*Leaf venation.*—Parallel, a color between 136B and 137A on upper surface, 137A on lower surface.

*Leaf margins.*—Entire, visibly smooth but serrated with very sharp short teeth are present that point in a forward direction.

*Leaf persistence.*—Evergreen in mild climates, dries but is persistent in colder regions.

*Leaf attachment.*—Sheathed, leaf is sheathed from the base of culm and the blade extends out from the culm at a ligule.

*Leaf blade size.*—Average of 77 cm in length and 8.5 mm in width tapering to a point at the apex.

*Leaf surface.*—Glabrous but slightly glossy on upper and lower surface.

*Leaf number.*—Average of 8 per culm.

*Leaf arrangement.*—Alternate, 2 ranked.

*Leaf blade color.*—Young leaves, upper surface; 138A to 138B with tips 138A, young leaves, lower surface; 138A, mature leaves, upper surface; color between 136B and 137A, mature leaves, lower surface; 137A.

*Leaf shaft color.*—147C tinted at base with 200B.

Flower description:

*General description.*—Feathery panicle terminating from each culm in early August through late October in Germany, comprised of numerous pistillate spikelets enclosed by hair-like lemmas.

*Fragrance.*—None.

*Panicle size.*—Average of 44 cm in length and 13.8 cm in width.

*Panicle color.*—Silvery white, closest to N155A.

*Rachis description.*—Strong, 138A in color, average of 82 cm in length and 1.5 cm in width, held upright or nearly so, internodes jointed.

*Spikelet description.*—Several flowered, pistillate, glumes longer than lower florets, surrounded by lemmas bearing a long awn.

*Spikelet number.*—About 20,000 per panicle.

*Spikelet size.*—About 5 mm in length and 1 mm in width.

*Glume.*—1 per spikelet, about 2 cm in length and 1 mm in width, 156D in color, linear in shape.

*Lemma.*—Numerous, about 50 per spikelet, hair-like, about 2 mm in length and 0.1 mm in width, 196C to 196D in color.

Reproductive organs:

*Androecium.*—Not present, pistillate florets only.

*Gynoecium.*—1 Pistil, 2 stigmas, 2, are feathery and 145D in color, ovary is superior, minute and 146D in color.

*Caryopsis.*—No caryopsis production was observed.

I claim:

1. A new and distinct cultivar of *Cortaderia* plant named 'Evita' as herein illustrated and described.

* * * * *